United States Patent
Knutson et al.

(10) Patent No.: US 10,501,090 B1
(45) Date of Patent: Dec. 10, 2019

(54) CANNABIS TESTING SYSTEM

(71) Applicants: James Kenneth Knutson, Sherwood Park (CA); Sarah Elise Knutson, Sherwood Park (CA)

(72) Inventors: James Kenneth Knutson, Sherwood Park (CA); Sarah Elise Knutson, Sherwood Park (CA)

(*) Notice: Subject to any disclaimer, the term of this patent is extended or adjusted under 35 U.S.C. 154(b) by 0 days.

(21) Appl. No.: 16/224,744

(22) Filed: Dec. 18, 2018

(51) Int. Cl.
| | | |
|---|---|---|
| *B60W 40/09* | (2012.01) | |
| *A61B 5/00* | (2006.01) | |
| *G06Q 50/26* | (2012.01) | |

(52) U.S. Cl.
CPC ........... *B60W 40/09* (2013.01); *A61B 5/4845* (2013.01); *G06Q 50/26* (2013.01); *B60W 2540/22* (2013.01); *B60W 2540/24* (2013.01)

(58) Field of Classification Search
CPC ............. B60W 40/09; B60W 2540/24; B60W 2540/22; G06Q 50/26; A61B 5/4845; G09B 19/167
See application file for complete search history.

(56) References Cited

U.S. PATENT DOCUMENTS

| | | | | |
|---|---|---|---|---|
| 5,717,776 A | * | 2/1998 | Watanabe | G06Q 20/341 |
| | | | | 235/380 |
| 10,115,173 B1 | * | 10/2018 | Manzella | G06Q 50/26 |
| 2008/0254417 A1 | * | 10/2008 | Mohamed | G09B 9/04 |
| | | | | 434/69 |
| 2011/0304465 A1 | * | 12/2011 | Boult | B60K 28/06 |
| | | | | 340/576 |
| 2011/0307188 A1 | * | 12/2011 | Peng | G06Q 10/0639 |
| | | | | 702/33 |
| 2013/0006674 A1 | * | 1/2013 | Bowne | H04W 4/40 |
| | | | | 705/4 |
| 2017/0105669 A1 | * | 4/2017 | Valenti | A61B 3/02 |

* cited by examiner

*Primary Examiner* — Ryan W Sherwin
(74) *Attorney, Agent, or Firm* — Golf Coast Intellectual Property Group

(57) ABSTRACT

A *Cannabis* testing system that is operable to provide competent demonstration of motor vehicle operation subsequent administration of an amount of *Cannabis*. The *Cannabis* testing system of the present invention includes monitored administration of an amount of *Cannabis* to an individual. The individual will utilize a test vehicle to perform motor vehicle tests prior to *Cannabis* administration. Ensuing performance of the initial motor vehicle tests the individual has administered thereto an amount of *Cannabis*. The amount of *Cannabis* present in the individual is measured in either a blood or urine test. The individual performs a second set of motor vehicle tests wherein the second set of motor vehicle tests are identical to the first set of motor vehicle tests. A comparison of the two motor vehicle tests are made and based on the results of the comparison a certificate and endorsement are provided to the individual.

20 Claims, 2 Drawing Sheets

CANNABIS TESTING SYSTEM

FIELD OF THE INVENTION

The present invention relates generally to chemical testing, more specifically but not by way of limitation, a testing system having a protocol operable to establish certification of the ability to operate machinery such as but not limited to a motor vehicle subsequent intake of an amount of *Cannabis*.

BACKGROUND

*Cannabis* consumption has grown rapidly over the past decade. Many states in the United States have now legalized *Cannabis* consumption for recreational use and medical use. Additionally, entire countries such as but not limited to Canada have formally legalized the consumption of *Cannabis*. The intake of *Cannabis* is similar to that of other drugs wherein alteration of an individual's ability to execute physical tasks could be limited based on the amount ingested. Intake of *Cannabis* is done in many forms such as but not limited to oils, edibles and inhalation.

As with other chemical substances, such as but not limited to alcohol, legal limits of the amount present within the bloodstream of an individual have been established. As is known in the art, the presence of alcohol at a level of 0.08% in the blood is the predetermined amount in which once exceeded a person is considered to be impaired. Any individual that has a blood alcohol amount exceeding the aforementioned amount is legally prohibited from operating a motor vehicle. *Cannabis* intake parallels that of alcohol wherein there is a certain amount of *Cannabis* that can be ingested by an individual and their ability to operate a motor vehicle is unimpaired. Current protocols and/or systems do not provide the ability to test and certify the ability for an individual to ingest *Cannabis* and then be legally certified to operate a vehicle.

Accordingly, there is a need for a *Cannabis* testing system that establishes testing protocols of an individual conducted subsequent ingestion of *Cannabis* wherein the system of the present invention includes but is not limited to the execution of tasks and the production of a certification to operate a motor vehicle.

SUMMARY OF THE INVENTION

It is the object of the present invention to provide a *Cannabis* testing system that is operable to provide certification of an individual to operate a motor vehicle subsequent ingestion of *Cannabis* wherein the system includes a testing facility that provides a venue to conduct various motor skills tests.

Another object of the present invention is to provide a *Cannabis* testing system that is operable to certify individuals to operate a motor vehicle subsequent ingestion of *Cannabis* wherein the system further includes a server database configured to store and provide certifications.

A further object of the present invention is to provide a *Cannabis* testing system that is operable to provide certification of an individual to operate a motor vehicle subsequent ingestion of *Cannabis* wherein the system of the present invention includes a step for monitoring an ingestion amount of *Cannabis*.

Still another object of the present invention is to provide a *Cannabis* testing system that is operable to certify individuals to operate a motor vehicle wherein the system provides a certification via an endorsement on a license or a motor vehicle plate.

An additional object of the present invention is to provide a *Cannabis* testing system that is operable to provide certification of an individual to operate a motor vehicle subsequent ingestion of *Cannabis* wherein the system provides an individualized set point of *Cannabis* level in either the blood or urine.

Yet a further object of the present invention is to provide a *Cannabis* testing system that is operable to certify individuals to operate a motor vehicle wherein the system of the present invention includes a set of standardized motor vehicle skills operation tests.

Another object of the present invention is to provide a *Cannabis* testing system that is operable to provide certification of an individual to operate a motor vehicle subsequent ingestion of *Cannabis* wherein the system provides administration of the *Cannabis* to the individual being tested.

An alternate object of the present invention is to provide a *Cannabis* testing system that is operable to certify individuals to operate a motor vehicle wherein the individual is charged a fee to complete the certification process of the system of the present invention.

Still a further object of the present invention is to provide a *Cannabis* testing system that is operable to provide certification of an individual to operate a motor vehicle subsequent ingestion of *Cannabis* wherein the system determines weight limits for the amount of *Cannabis* that an individual can ingest and still demonstrate successful operation of a motor vehicle.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
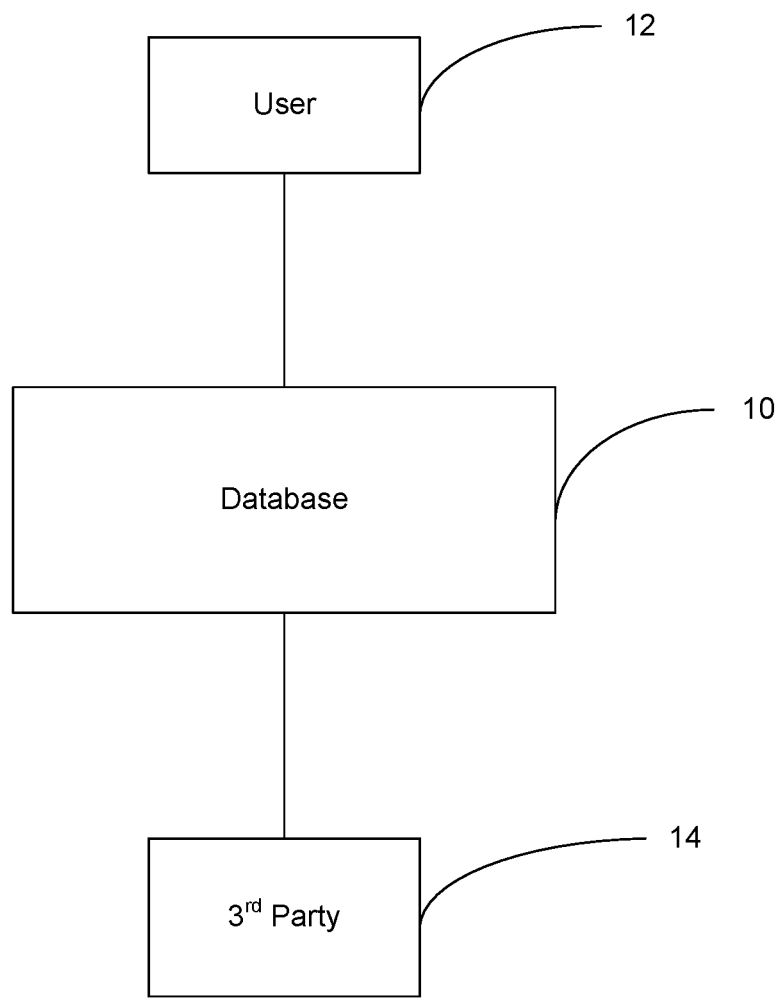
FIG. 1 is block diagram of the server database of the present invention.

Referring now to the drawings submitted herewith, wherein various elements depicted therein are not necessarily drawn to scale and wherein through the views and figures like elements are referenced with identical reference numerals, there is illustrated a *Cannabis* testing system 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted herewith, the *Cannabis* testing system 100 includes an online server database 10 that is a computer server having the necessary electronics to receive, store, transmit and manipulate data. The server database 10 includes software that facilitates access thereto and operation of the server database 10. The server database 10 is operably coupled to the Internet utilizing suitable communication protocols and is established within the scope of the present invention to provide access to certification records for both users 12 and any authorized third party 14. It is contemplated within the scope of the present invention that the *Cannabis* testing system 100 could have more than one server database 10 and be accessible by a plurality of users 12 and third parties 14.

Figure 2:
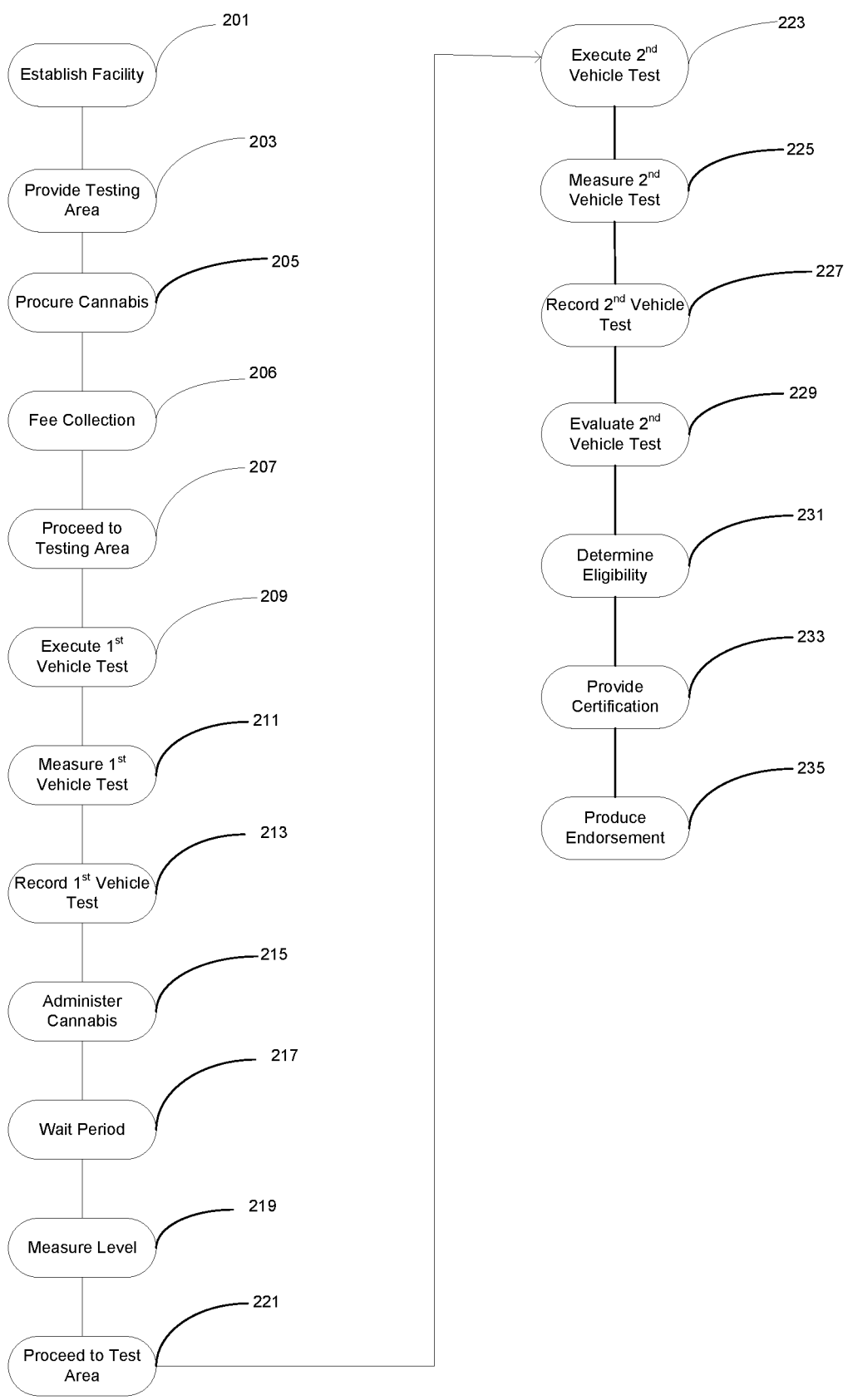
FIG. 2 is a process flowchart of the testing and certification produced by the system of the present invention.

Referring now in particular to FIG. 2, the process of the *Cannabis* testing system 100 is outlined therein. In step 201, a *Cannabis* testing facility is established. It is contemplated within the scope of the present invention that the *Cannabis* testing facility could be either a governmental organization or an authorized third party organization. The *Cannabis* testing facility would include but is not limited to administration offices and a testing lab with equipment. Step 203, a testing area is provided to perform and execute motor vehicle tests. In the testing area, an individual will perform the first motor vehicle tests and the second motor vehicle tests. It should be understood within the scope of the present invention that the testing area could be monitored by both staffed individuals as well as the necessary computer equipment and cameras required to facilitate and record the execution of the motor vehicle tests. In step 205, the organization operating the *Cannabis* testing system 100 engages in the necessary protocols so as to acquire a desired amount of *Cannabis* to be administered to individuals seeking to obtain certification from the *Cannabis* testing system 100. Step 206, any individual desiring to be tested by the operator of the *Cannabis* testing system 100 will pay a fee to the operator of the *Cannabis* testing system 100. Step 207, subsequent arrival to the *Cannabis* testing facility an individual will proceed to the motor vehicle testing area wherein the motor vehicle testing area includes test vehicles that will be operated by the individual.

In step 209, the individual will perform a plurality of first motor vehicle tests. It is contemplated within the scope of the present invention that the plurality of tests performed as part of the *Cannabis* testing system 100 will include but are not limited to: course navigation, vehicle stop tests and vehicle acceleration test. It should be understood within the scope of the present invention that the plurality of tests are established and standardized wherein every individual being tested by the *Cannabis* testing system 100 will perform the same tests on the same vehicle in order to establish a proper baseline protocol. Step 211, the first vehicle tests are measured utilizing the necessary equipment such as but not limited to cameras, computers and other measurement instrumentation. In step 213, the first vehicle tests are recorded wherein the first vehicle tests are established so as to provide a baseline for operation of the motor vehicle by an individual wherein the first vehicle tests are performed prior to ingestion of *Cannabis*.

In step 215, the operator of the *Cannabis* testing system 100 will administer to an individual a standard dosage of *Cannabis*. It should be understood that the administration of the *Cannabis* could occur via smoking or ingestion by other means. While no particular dosage of administration is required, it is desired within the scope of the present invention that the administration of *Cannabis* be delivered via smoking and that the amount of *Cannabis* is between one half and two grams of *Cannabis*. Step 217, ensuing administration of the *Cannabis*, the individual will be required to wait in order for the administration to have time for complete neurological effect. While no particular time is required, it is desired within the scope of the *Cannabis* testing system 100 that the waiting period be within the range of five minutes to thirty minutes to allow the neurological effect to have an impact on the individual. In step 219, the *Cannabis* level for the individual will be measured so as to establish the concentration present in the individual subsequent administration of *Cannabis*. It is contemplated within the scope of the present invention that the *Cannabis* level could be measured utilizing either blood or urine testing.

Subsequent the measuring of the *Cannabis* level, the individual will proceed to the vehicle test area in step 221. Step 223, the user will utilize the exact vehicle in which the user performed the first vehicle test to perform the second vehicle tests. The second vehicle tests are identical to that of the first vehicle tests. In step 225, the second vehicle tests are measure utilizing the same equipment with which the first vehicle tests were measured. Step 227, the second vehicle tests are recorded by the operator of the *Cannabis* testing system 100. In step 229, the operator of the *Cannabis* testing system 100 will evaluate and compare the results of the first vehicle tests and the second vehicle tests and identify any differences amongst the test scores. It is contemplated within the scope of the present invention that if the second vehicle test are cumulatively deficient as compared to the first vehicle tests by a percentage of more than ten percent than the individual will not be provided a certification to operate a motor vehicle while have *Cannabis* in their system. It should be understood that while a ten percent difference is desired within the scope of the present invention, the cumulative difference between the first vehicle tests and second vehicle tests could range from five to twenty-five percent.

In step 231, the operator of the *Cannabis* testing system 100 will determine eligibility to operate a motor vehicle subsequent ingestion of *Cannabis* based on the aforementioned test comparison. Step 233, if an individual has an acceptable deviation between the first motor vehicle tests and the second motor vehicle tests, the operator of the *Cannabis* testing system 100 produces and provides to the individual a certification for motor vehicle operation wherein the certification provides either blood or urine concentration levels at which the individual has demonstrated competent operation of a motor vehicle. Step 235, and endorsement is produced by the operator of the *Cannabis* testing system 100 wherein the endorsement can include but is not limited to an identification of the drivers license or on the motor vehicle plate of the individual who successfully completed the testing protocol of the *Cannabis* testing system 100.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A *Cannabis* testing system operable to provide demonstration of competent motor vehicle operation subsequent ingestion of *Cannabis* comprising the steps of:
    establishing a testing facility;
    providing a motor vehicle testing area;
    executing a set of first motor vehicle tests;
    measuring the first motor vehicle tests;
    recording the first motor vehicle tests;
    administering *Cannabis* to a user that has completed the first motor vehicle tests;
    executing a set of second motor vehicle tests, wherein the second motor vehicle tests are identical to the first motor vehicle tests;
    measuring the second motor vehicle tests;
    comparing results from the first motor vehicle tests and the second motor vehicle tests;
    determining eligibility for motor vehicle operation; and
    providing a certification for operation of a motor vehicle subsequent ingestion of *Cannabis*.

2. The *Cannabis* testing system as recited in claim 1, and further including the step of waiting to complete the second motor vehicle tests, wherein an individual is required to wait at least thirty minutes prior to executing the second motor vehicle tests.

3. The *Cannabis* testing system as recited in claim 2, wherein administration of the *Cannabis* is performed at a level of one half gram to two grams.

4. The *Cannabis* testing system as recited in claim 3, and further including the step of collecting a fee, wherein an operator of the *Cannabis* testing system will collect a fee from an individual desiring to be tested.

5. The *Cannabis* testing system as recited in claim 4, wherein the first motor vehicle tests and second motor vehicle tests including stopping procedures from various speeds.

6. The *Cannabis* testing system as recited in claim 5, wherein the first motor vehicle tests and second motor vehicle tests are performed on an identical vehicle.

7. The *Cannabis* testing system as recited in claim 6, and further including the step of measuring the *Cannabis* level in an individual, wherein measurement of the *Cannabis* level is performed via blood or urine specimen.

8. A *Cannabis* testing system operable to prove competent motor vehicle operation for an individual that has ingested *Cannabis* wherein the *Cannabis* testing system comprises the steps of:
    establishing a testing facility;
    providing a motor vehicle testing area, wherein the motor vehicle testing area is sufficient to operate a motor vehicle within and perform various driving procedures;
    collecting a fee, wherein an individual seeking certification by the *Cannabis* testing system pays a fee to an operator of the *Cannabis* testing system;
    executing a set of first motor vehicle tests, said first motor vehicle tests being performed utilizing a test vehicle;
    measuring the first motor vehicle tests;
    recording the first motor vehicle tests;
    administering *Cannabis* to a user that has completed the first motor vehicle tests;
    measuring *Cannabis* levels present in the individual;
    executing a set of second motor vehicle tests, wherein the second motor vehicle tests are identical to the first motor vehicle tests, wherein the second motor vehicle tests are performed utilizing the test vehicle used to perform the first motor vehicle tests;
    measuring the second motor vehicle tests;
    comparing results from the first motor vehicle tests and the second motor vehicle tests;
    determining eligibility for motor vehicle operation; and
    providing a certification for operation of a motor vehicle subsequent ingestion of *Cannabis*.

9. The *Cannabis* testing system as recited in claim 8, and further including the step of waiting a time period to perform the second motor vehicle tests.

10. The *Cannabis* testing system as recited in claim 9, wherein the step of waiting a time period to perform the second motor vehicle tests is within a time range of five minutes to thirty minutes.

11. The *Cannabis* testing system as recited in claim 10, and further including the step of producing an endorsement, wherein the operator of the *Cannabis* testing system produces an endorsement for an individual to operate a motor vehicle having ingested an amount of *Cannabis*.

12. The *Cannabis* testing system as recited in claim 11, wherein the endorsement is provided on a drivers license of the individual or a motor vehicle plate.

13. The *Cannabis* testing system as recited in claim 12, wherein administration of the *Cannabis* is performed at a level of one half gram to two grams.

14. The *Cannabis* testing system as recited in claim 13, wherein the step of comparing results from the first motor vehicle tests and the second motor vehicle tests must be within ten percent in order for an individual to receive a certification from the *Cannabis* testing system.

15. A *Cannabis* testing system operable to prove competent motor vehicle operation for an individual that has ingested *Cannabis* wherein the *Cannabis* testing system comprises the steps of:

establishing a testing facility;

providing a motor vehicle testing area, wherein the motor vehicle testing area is sufficient to operate a motor vehicle within and perform various driving procedures;

collecting a fee, wherein an individual seeking certification by the *Cannabis* testing system pays a fee to an operator of the *Cannabis* testing system;

executing a set of first motor vehicle tests, said first motor vehicle tests being performed utilizing a test vehicle;

measuring the first motor vehicle tests;

recording the first motor vehicle tests;

administering *Cannabis* to a user that has completed the first motor vehicle tests;

waiting a time period to perform second motor vehicle tests;

measuring *Cannabis* levels present in the individual;

executing a set of second motor vehicle tests, wherein the second motor vehicle tests are identical to the first motor vehicle tests, wherein the second motor vehicle tests are performed utilizing the test vehicle used to perform the first motor vehicle tests;

measuring the second motor vehicle tests;

comparing results from the first motor vehicle tests and the second motor vehicle tests;

determining eligibility for motor vehicle operation; and providing a certification for operation of a motor vehicle subsequent ingestion of *Cannabis*; and producing an endorsement, wherein the operator of the *Cannabis* testing system produces an endorsement for an individual to operate a motor vehicle having ingested an amount of *Cannabis*.

16. The *Cannabis* testing system as recited in claim 15, wherein administration of the *Cannabis* is performed at a level of one half gram to two grams and wherein the individual ingests the *Cannabis* via smoking.

17. The *Cannabis* testing system as recited in claim 16, wherein the step of comparing results from the first motor vehicle tests and the second motor vehicle tests must be within ten percent in order for an individual to receive a certification from the *Cannabis* testing system.

18. The *Cannabis* testing system as recited in claim 17, wherein the endorsement is provided on a drivers license of the individual or a motor vehicle plate.

19. The *Cannabis* testing system as recited in claim 18, wherein the step of waiting a time period to perform second motor vehicle tests is from five minutes to thirty minutes.

20. The *Cannabis* testing system as recited in claim 19, wherein the step of measuring *Cannabis* levels present in the individual includes measurement of the *Cannabis* level in a blood or urine specimen of the individual.

\* \* \* \* \*